United States Patent
Yoshida et al.

(10) Patent No.: US 12,171,602 B2
(45) Date of Patent: Dec. 24, 2024

(54) OPERATION DEVICE AND X-RAY DIAGNOSIS SYSTEM

(71) Applicant: CANON MEDICAL SYSTEMS CORPORATION, Otawara (JP)

(72) Inventors: Hajime Yoshida, Nasushiobara (JP); Keisuke Sugawara, Otawara (JP); Hiroshi Yoshida, Yaita (JP); Yusuke Narabu, Nasushiobara (JP); Akio Tetsuka, Shioya-gun (JP); Shingo Abe, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 515 days.

(21) Appl. No.: 17/454,356

(22) Filed: Nov. 10, 2021

(65) Prior Publication Data

US 2022/0142596 A1    May 12, 2022

(30) Foreign Application Priority Data

Nov. 12, 2020 (JP) ................ 2020-188985

(51) Int. Cl.
 *A61B 6/00* (2024.01)
 *A61B 6/46* (2024.01)
 *G06F 3/01* (2006.01)

(52) U.S. Cl.
 CPC .......... *A61B 6/467* (2013.01); *A61B 6/547* (2013.01); *G06F 3/011* (2013.01)

(58) Field of Classification Search
 CPC ......... A61B 6/4441; A61B 6/467; A61B 6/54; A61B 6/547; A61B 6/548
 See application file for complete search history.

(56) References Cited

U.S. PATENT DOCUMENTS 9,750,476 B2    9/2017  Ishii et al.
2015/0250439 A1*  9/2015  Ishii ................... A61B 6/54
                                                        378/115

FOREIGN PATENT DOCUMENTS

| JP | 8-206083 A | 8/1996 |
|---|---|---|
| JP | 2007-296177 A | 11/2007 |
| JP | 2009-022602 A | 2/2009 |
| JP | 2015-180242 A | 10/2015 |
| JP | 2016-52429 A | 4/2016 |
| JP | 2018-32130 A | 3/2018 |
| JP | 2018-198650 A | 12/2018 |
| WO | WO 2020/121536 A1 | 6/2020 |

OTHER PUBLICATIONS

Japanese Office Action issued Apr. 23, 2024 in Japanese Patent Application No. 2020-188985, citing documents 15-19 therein, 4 pages.

\* cited by examiner

*Primary Examiner* — Dani Fox
(74) *Attorney, Agent, or Firm* — Oblon, McClelland, Maier & Neustadt, L.L.P.

(57) ABSTRACT

An operation device comprises a detector configured to detect an operation on a virtual switch by an operator to operate an X-ray irradiation in an X-ray diagnosis apparatus, wherein the virtual switch is virtually set at a position settled relatively with respect to the operator and output circuitry configured to output a detection result of the operation detected by the detector to the X-ray diagnosis apparatus to be operated. This device eliminates the need for looking away from a display monitor every time the operator operates the X-ray diagnosis apparatus.

18 Claims, 19 Drawing Sheets

TB1 : USER INFORMATION TABLE

| USER ID : A 1 2 3 4 5 ||
|---|---|
| QUANTITY OF PEDAL | 3 |
| SIZE OF PEDAL | MEDIUM |
| LAYOUT OF PEDAL | PATTERN A |

FIG. 12

OPERATION DEVICE AND X-RAY DIAGNOSIS SYSTEM

CROSS REFERENCE TO RELATED APPLICATIONS

This application is based upon and claims the benefit of priority from the prior Japanese Patent Application No. 2020-188985, filed on Nov. 12, 2020, the entire contents of which are incorporated herein by reference.

FIELD

Embodiments described herein and illustrated in the accompanying drawings relate to an operation device and an X-ray diagnosis system.

BACKGROUND

X-ray diagnosis apparatuses are modality that enables the inside of subjects to be observed by irradiating the subjects or patients with X-ray so that X-ray detectors can detect X-ray doses transmitted through the subjects. Various tissues are able to be photographed with X-ray because the X-ray doses transmitted through the subjects vary depending on each tissue of the subjects. Such X-ray diagnosis apparatuses can be used along with foot switches that serve as input devices to receive input operations, from operator, to indicate X-ray irradiation.

In addition, X-ray photograph using contrast medium and so on, enables simultaneous observation of various aspects of different tissues and organs including bloodstream, alimentary canal and urinary system, and has been widely used for medical purposes such as diagnosis and surgery. When an X-ray diagnosis apparatus is used for angiographic examination or intravascular treatment and so on, an operator inserts a guide wire, a catheter and other devices for intravascular treatment through a blood vessel of the subject up to a prescribed position and then moves a C-arm to readjust and place a body portion to be examined in a suitable position, while checking with a display monitor the whole time.

In process of such diagnosis of the subjects or procedures for treatment using the X-ray diagnosis apparatus, the operator would rather not look away from the display monitor to keep the procedures proper and quick.

However, because its foot switch is set on the floor, the operator is required to look away from the display monitor to check the location of the foot switch around the feet. Further, a pedal of the foot switch may not be even detectable from the operator because it is often covered with a drape and so on.

BRIEF DESCRIPTION OF THE DRAWINGS

FIG. 12 is a diagram illustrating an example of a configuration of user information tables stored by the wearable device controller in the X-ray diagnosis system according to the first embodiment.

DETAILED DESCRIPTION

Embodiments of an operation device and an X-ray diagnosis system will now be described in detail with reference to the accompanying drawings. Note that, in the following descriptions, elements having substantially the same function and configuration are assigned to the same numerical symbols, and the descriptions will not be repeated unless it is necessary.

First Embodiment

An operation device and an X-ray diagnosis system according to a first embodiment will now be described. It should be noted that the overall configuration and motion will be described with an example that an X-ray diagnosis apparatus to be operated by the operation device is an apparatus for diagnosing circulatory system, however, the X-ray diagnosis apparatus for diagnosing other portions may also be operated by the operation device.

Figure 1:
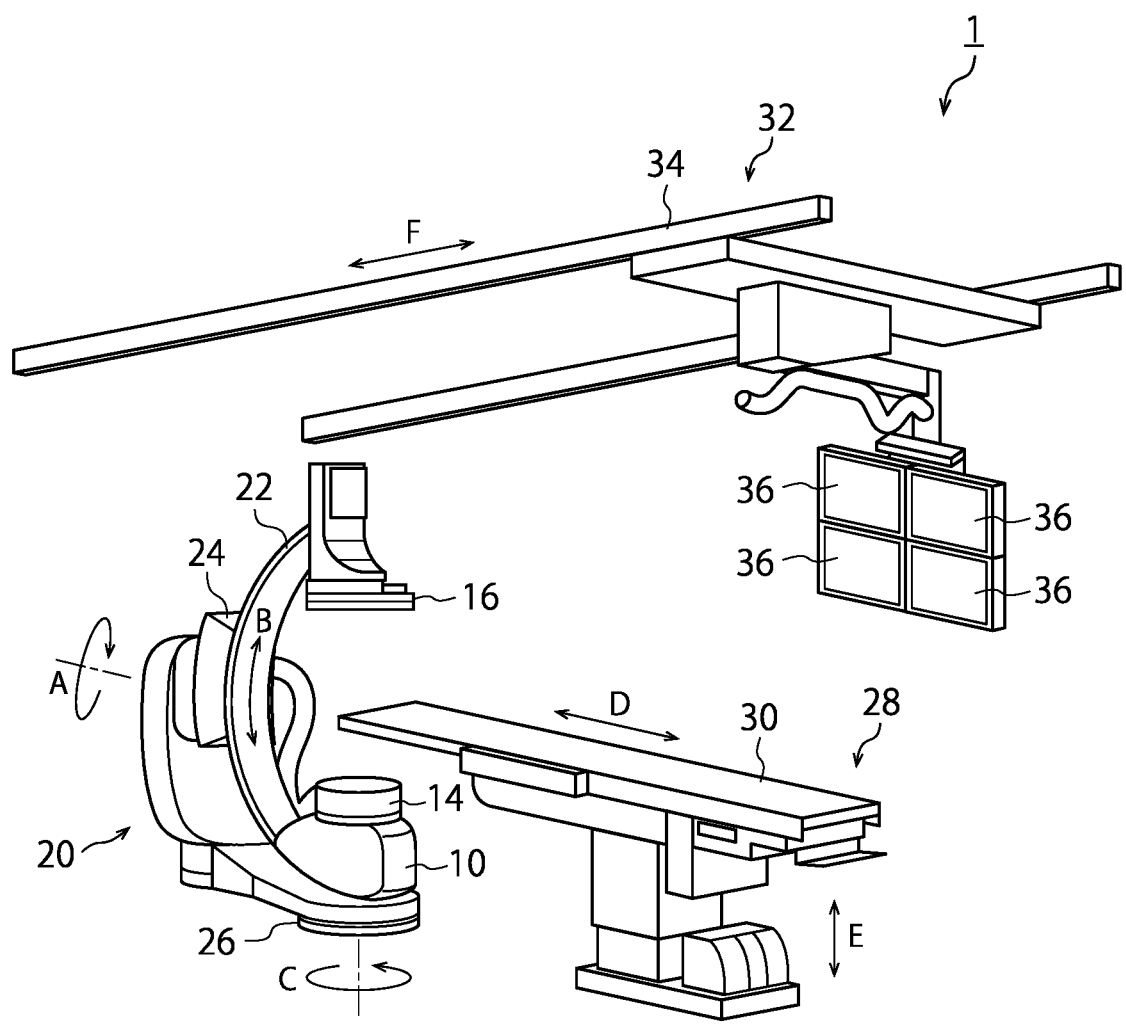
FIG. 1 is a perspective diagram illustrating an example of an overall configuration of an X-ray diagnosis apparatus according to a first embodiment.
Figure 2:
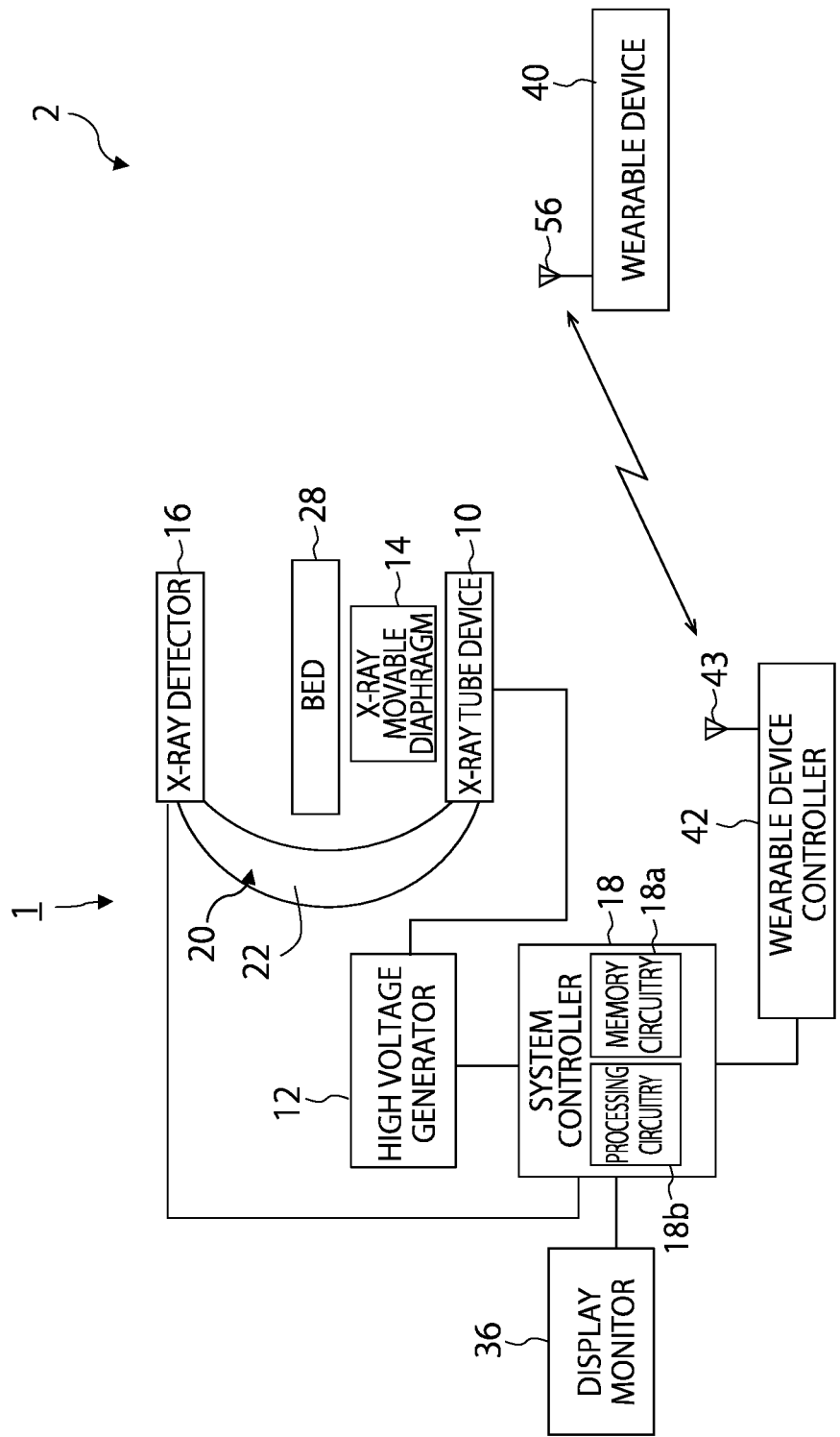
FIG. 2 is a block diagram illustrating an example of a configuration of an X-ray diagnosis system according to the first embodiment.

FIG. 1 is an external perspective diagram illustrating a configuration of an X-ray diagnosis apparatus 1 according to the present embodiment. FIG. 2 is a block diagram illustrating a configuration of an X-ray diagnosis system 2 having the X-ray diagnosis apparatus 1 in FIG. 1 and a wearable device 40.

As shown in FIG. 1, a voltage is applied to an X-ray tube device 10 by a high voltage generator 12 (shown in FIG. 2) to generate X-ray. An X-ray movable diaphragm 14 has a function for adjusting irradiation range of X-ray generated by the X-ray tube device 10. For example, the X-ray movable diaphragm 14 has two pairs of movable blades to adjust the irradiation range of X-ray by opening and closing each pair of the movable blades.

For example, an X-ray detector 16 has a Flat Panel Detector (FPD) to detect X-ray irradiated to the X-ray detector 16. Based on this detected X-ray, the X-ray detector 16 generates image data for X-ray fluoroscopic image or X-ray photograph image. The generated image data is output to a system controller 18 (shown in FIG. 2).

A holding device 20 has a holding part 24, and the holding part 24 holds C-arm 22. The X-ray tube device 10 is provided on one end of the C-arm 22 and the X-ray detector 16 is provided on the other end of the C-arm 22. Since the C-arm 22 has a curved shape, the X-ray detector 16 is equipped so as to face the X-ray tube device 10. This allows the X-ray detector 16 to detect X-ray irradiated by the X-ray tube device 10. The holding part 24 of the holding device 20 is rotatable in the direction of an arrow A while holding the C-arm 22. When the holding part 24 rotates, the C-arm 22 held by the holding part 24 also rotates in the direction of the arrow A. In addition, the holding part 24 holds the C-arm 22 slidably in the direction of an arrow B along the arc. Furthermore, the holding device 20 is rotatable in the direction of an arrow C, centering a base 26. Independently of this rotation of the whole holding device 20 at the base 26, the X-ray detector 16 and the X-ray movable diaphragm 14 are rotatable in the direction of the arrow C.

A bed 28 has a top board 30, which is slidable in the direction of an arrow D with a subject laid thereon. Further, the top board 30 is elevatable in the up and down direction of an arrow E. A ceiling suspension part 32 has a ceiling running mechanism 34 and suspends display monitors 36 movably in the direction of an arrow F. In the present embodiment, for example, the ceiling suspension part 32 suspends four display monitors 36.

Further, as shown in FIG. 2, the X-ray diagnosis apparatus 1 according to the present embodiment constitutes the X-ray diagnosis system 2 by adding the wearable device 40. The wearable device 40 is a device to be worn on the operator. In the present embodiment, the wearable device 40 is worn on the right foot and the left foot of the operator for example. When the wearable device 40 is worn on the operator, the X-ray diagnosis system 2 detects motion of the operator for the X-ray diagnosis apparatus 1. Particularly, in the present embodiment, the X-ray diagnosis system 2 detects motion of the right foot and the left foot of the operator and determines the operation which the operator tries to perform on the X-ray diagnosis apparatus 1.

On the other hand, the X-ray diagnosis apparatus 1 according to the present embodiment further has a wearable device controller 42. The wearable device controller 42 is processing circuitry to control communication between the wearable device 40 and the system controller 18. The wearable device 40 worn on the operator is connected to the wearable device controller 42 in the X-ray diagnosis apparatus 1 through wireless communication such as Wi-Fi (registered trademark) and Bluetooth (registered trademark). In particular, such wireless communication connects between a signal transceiver 43 in the wearable device controller 42 and a signal transceiver 56 in the wearable device 40. Such wireless communication may connect between the wearable device 40 and the wearable device controller 42 without physically interrupting the operator wearing the wearable device 40. However, the wearable device 40 and the wearable device controller 42 may also be connected through wired communication.

For example, the wearable device controller 42 may be built in the lower part of the bed 28, or be stored inside of the main body of the X-ray diagnosis apparatus 1 in which the system controller 18 is also stored. The wearable device controller 42 transmits various signals from the X-ray diagnosis apparatus 1 to the wearable device 40 and also receives various signals from the wearable device 40. The wearable device controller 42 transmits and receives these signals under the control of the system controller 18.

The wearable device controller 42 further has a function for controlling the wearable device 40. For example, the wearable device controller 42 sets a virtual switch at a position settled relatively with respect to the operator and stores information on operational settings for the virtual switch respectively for a plurality of operators. The details will be described later. The function of the wearable device controller 42 for controlling the wearable device 40 may be provided in the X-ray diagnosis apparatus 1, or in the wearable device 40. Further, such function of the wearable device controller 42 for controlling the wearable device 40 may also be provided separately in both the X-ray diagnosis apparatus 1 and the wearable device 40. This wearable device controller 42 constitutes an operation device control circuitry in the present embodiment.

In the system controller 18, programs are read out from a memory circuitry 18A and executed by a processing circuitry 18B so that functions corresponding to each of the programs. The processing circuitry 18B has a processor. In other words, the processing circuitry 18B including the processor, which has already read out and executed each of the programs, has various functions necessary for controlling the X-ray diagnosis apparatus 1, in accordance with control signal received from the wearable device controller 42. It should be noted that the processing circuitry 18B in the system controller 18 may be implemented by a single processor, or may be implemented by combining a plurality of independent processors.

Figure 3:
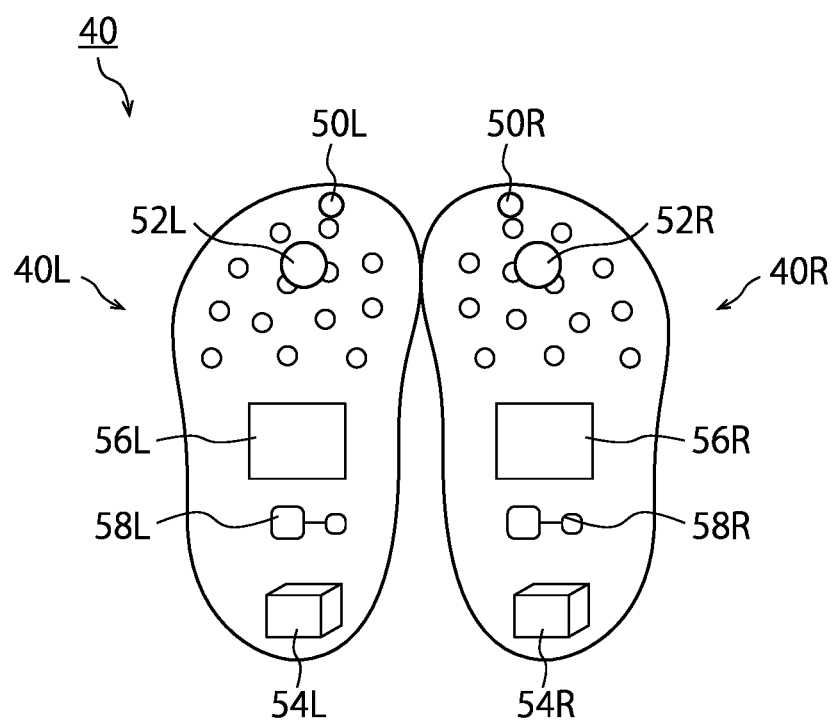
FIG. 3 is a diagram illustrating an example of a configuration of a wearable device according to the first embodiment.

FIG. 3 is a diagram illustrating an example of a configuration of the wearable device 40 according to the present embodiment. As shown in FIG. 3, the wearable device 40 in the present embodiment has a right device 40R worn on the right foot of the operator, and a left device 40L worn on the left foot of the operator. The right device 40R and the left device 40L are respectively configured as shoes or sandals that are worn on the operator, and a layout of various sensors on the soles is shown in FIG. 3. The wearable device 40 constitutes the operation device that is used for operating X-ray irradiation in the X-ray diagnosis apparatus 1 in the present embodiment.

The right device 40R and the left device 40L respectively have position detection elements 50R and 50L on the toe portions. For example, these position detection elements 50R and 50L are respectively configured by Global Positioning System (GPS) and are able to detect positions of the right device 40R and the left device 40L. For example, the positions may be detected by transmitting radar from the wearable device controller 42 to specify a distance and a direction from the wearable device controller 42 to the right device 40R and the left device 40L.

The right device 40R and the left device 40L respectively further have pressure sensors 52R and 52L in the vicinities of the thenar eminences. The pressure sensor 52R detects pressure when the operator steps on with the right foot, and the pressure sensor 52L detects pressure when the operator steps on with the left foot. These pressure sensors 52R and 52L may respectively have an analog output circuit element such as a piezoelectric element, or may employ a technique for automatically detecting a load and a stroke by a microswitch.

The right device 40R and the left device 40L respectively further have acceleration sensors 54R and 54L in the heel portions. The acceleration sensor 54R detects acceleration for motion of the right foot of the operator, and the acceleration sensor 54L detects acceleration for motion of the left foot of the operator. For example, these acceleration sensors 54R and 54L may respectively have a circuit element for detecting changes in resistance of a piezoelectric element and an electrostatic capacity.

The right device 40R and the left device 40L respectively further have signal transceivers 56R and 56L in the plantar arch portions. These signal transceivers 56R and 56L communicate with the wearable device controller 42. For example, the signal transceiver 56R transmits, to the wearable device controller 42, a detection signal to notify detection result from the position detection element 50R, the pressure sensor 52R or the acceleration sensor 54R in the right device 40R. On the other hand, the signal transceiver 56L transmits, to the wearable device controller 42, the detection signal to notify detection result from the position detection element 50L, the pressure sensor 52L and/or the acceleration sensor 54L in the left device 40L.

The right device 40R and the left device 40L respectively further have vibration devices 58R and 58L in the vicinities of the heel portions. These vibration devices 58R and 58L are respectively controlled in accordance with control signal received, from the wearable device controller 42, by the signal transceivers 56R and 56L. In other words, the wearable device controller 42 vibrates the vibration devices 58R and 58L spontaneously in accordance with the control signal.

In the present embodiment, the position detection elements 50R and 50L, the pressure sensors 52R and 52L, and the acceleration sensors 54R and 54L constitute a detector for detecting an operation on the virtual switch by the operator. Additionally, in the present embodiment, the transmission function of the signal transceivers 56R and 56L constitutes an output circuitry for outputting detection result of the operation to the X-ray diagnosis apparatus 1, and the reception function of the signal transceivers 56R and 56L constitutes a reception circuitry for receiving control signal from the X-ray diagnosis apparatus 1.

Figure 4:
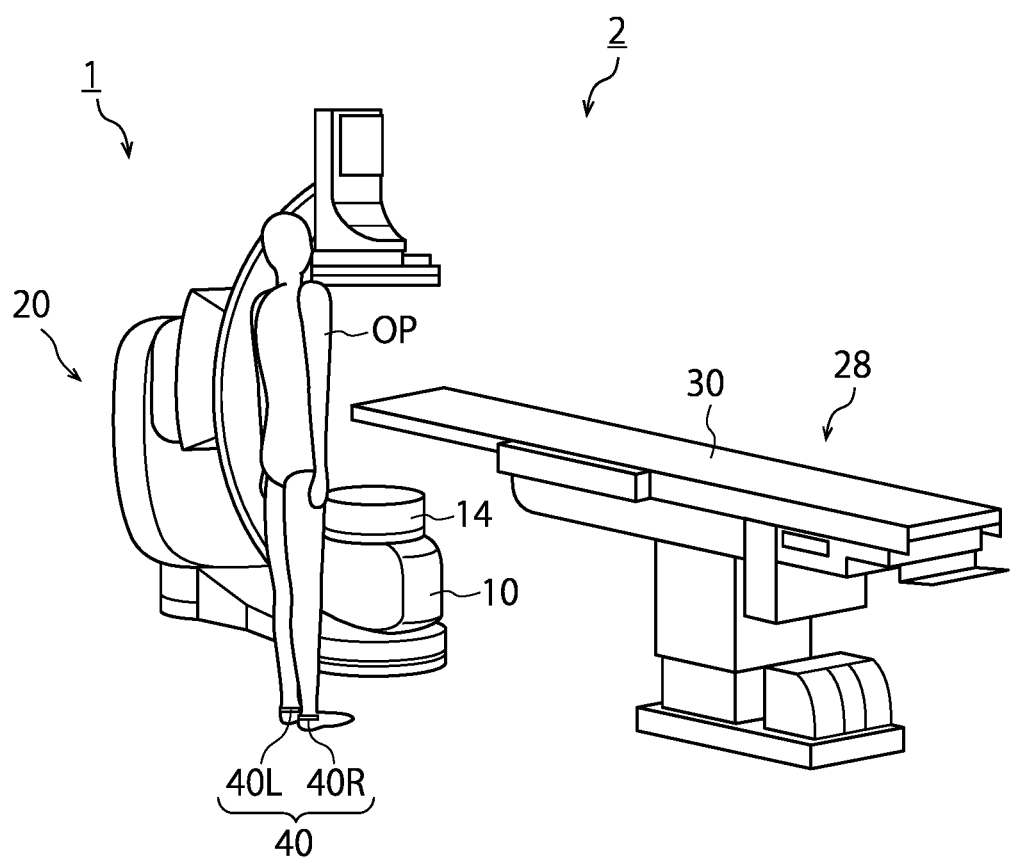
FIG. 4 is a perspective diagram illustrating an example of a position at which an operator stands during operation on the X-ray diagnosis apparatus in the X-ray diagnosis system according to the first embodiment.

FIG. 4 is a perspective diagram illustrating an example of a position at which the operator OP stands during the operation on the X-ray diagnosis apparatus 1 in the X-ray diagnosis system 2 according to the present embodiment. As shown in the FIG. 4, the operator OP operates the X-ray diagnosis apparatus 1 while standing in the vicinity of the bed 28. The operator OP operates the holding device 20 and the bed 28 while taking care of a subject laid on the top board 30 of the bed 28. Traditional X-ray diagnosis apparatuses have mechanically-constructed foot switch to execute these operations on the X-ray diagnosis apparatus 1, however, instead of such mechanical foot switch, the X-ray diagnosis apparatus 1 according to the present embodiment has a virtual foot switch set by the wearable device controller 42. Setting such virtual foot switch eliminates the need for looking away from the display monitor 36 to check the location of the foot switch, and for paying attention to the foot switch interfering with the X-ray diagnosis apparatus 1.

Figure 5:
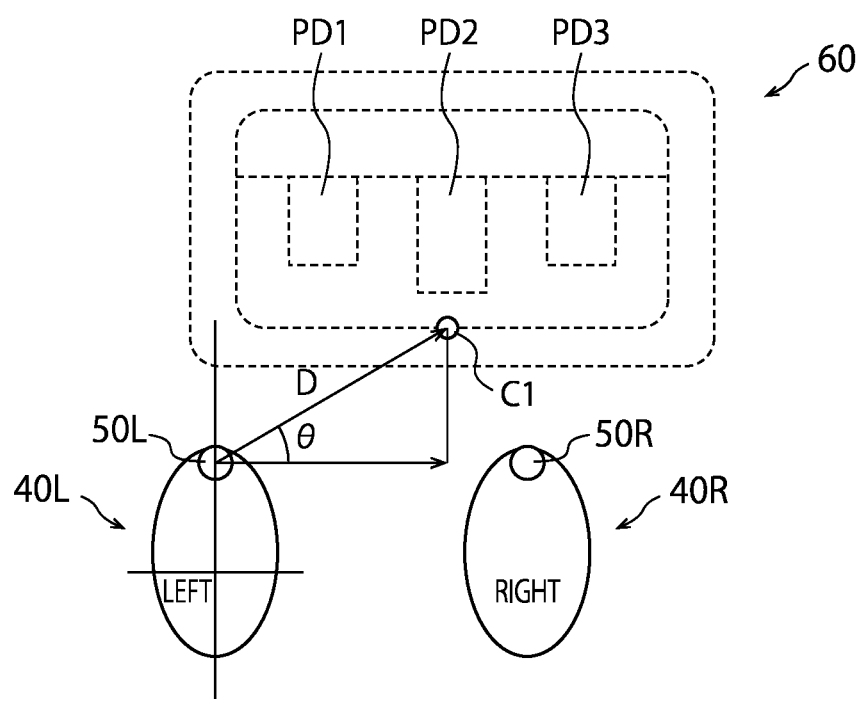
FIG. 5 is a diagram illustrating an example of a layout of a virtual foot switch set by the X-ray diagnosis system according to the first embodiment.

FIG. 5 is a diagram illustrating an example of a layout of a foot switch 60 virtually set by the X-ray diagnosis system 2 according to the present embodiment. The foot switch 60 is a virtual switch and thus impalpable. This means that the operator steps on pedal of the foot switch 60 as if there were a physical foot switch. In the present embodiment, the foot switch 60 is used for operating X-ray irradiation in the X-ray diagnosis apparatus 1 for example.

In the example of FIG. 5, the left foot of the operator is the pivot foot. The foot switch 60 is virtually set in the two o'clock direction of the left foot or the pivot foot. A position at which the foot switch 60 is set is determined by presetting the distance and direction from the foot switch 60 with respect to the pivot foot. In particular, a position of the position detection element 50L attached to the left device 40L of the pivot foot serves as the reference position, or the so-called origin. For example, the direction in which the foot switch 60 is set may be defined as an angle θ. Further, for example, the distance from the reference position to the foot switch 60 may be defined as a distance D. Here, the distance D is from the reference position to a lower part center C1 of the foot switch 60. This is how the virtual foot switch 60 is set at a position settled relatively with respect to the operator.

It should be noted that, because the pivot foot can be different depending on the operator, the pivot foot is optionally changeable in the X-ray diagnosis system 2 according to the present embodiment. In other words, the right foot can also be set as the pivot foot in the X-ray diagnosis system 2. For convenience of explanation, however, the following descriptions will be explained with an example that the left foot of the operator is the pivot foot and the right foot is the body portion for operating the foot switch 60.

In the present embodiment, the virtually set foot switch 60 has three virtual pedals PD1, PD2 and PD3. For example, the pedal PD1 is stepped on when the operator executes X-ray photograph to obtain X-ray image, and the pedal PD2 is stepped on when the operator executes X-ray fluoroscopy to obtain simultaneous X-ray fluoroscopic image, and the pedal PD3 is stepped on when the operator operates the bed 28. It should be noted that the number and the function of the virtual pedals of the virtual foot switch 60 are optionally changed. They may be changed in accordance with the X-ray diagnosis apparatus 1 or with personal preference of the operator. The size of each pedal may also be changed in accordance with its function or with personal preference of the operator.

Further, in the X-ray diagnosis system 2 according to the present embodiment, the pivot foot that the operator puts the weight on, and the dominant foot for operating the pedals are optionally changeable. For example, the operator can pre-set the pivot foot and the dominant foot for operating in the wearable device controller 42. In this setting, the operator may set the pivot foot, the dominant foot for operating or both the pivot foot and the dominant foot in the wearable device controller 42 in the X-ray diagnosis system 2.

Figure 6:
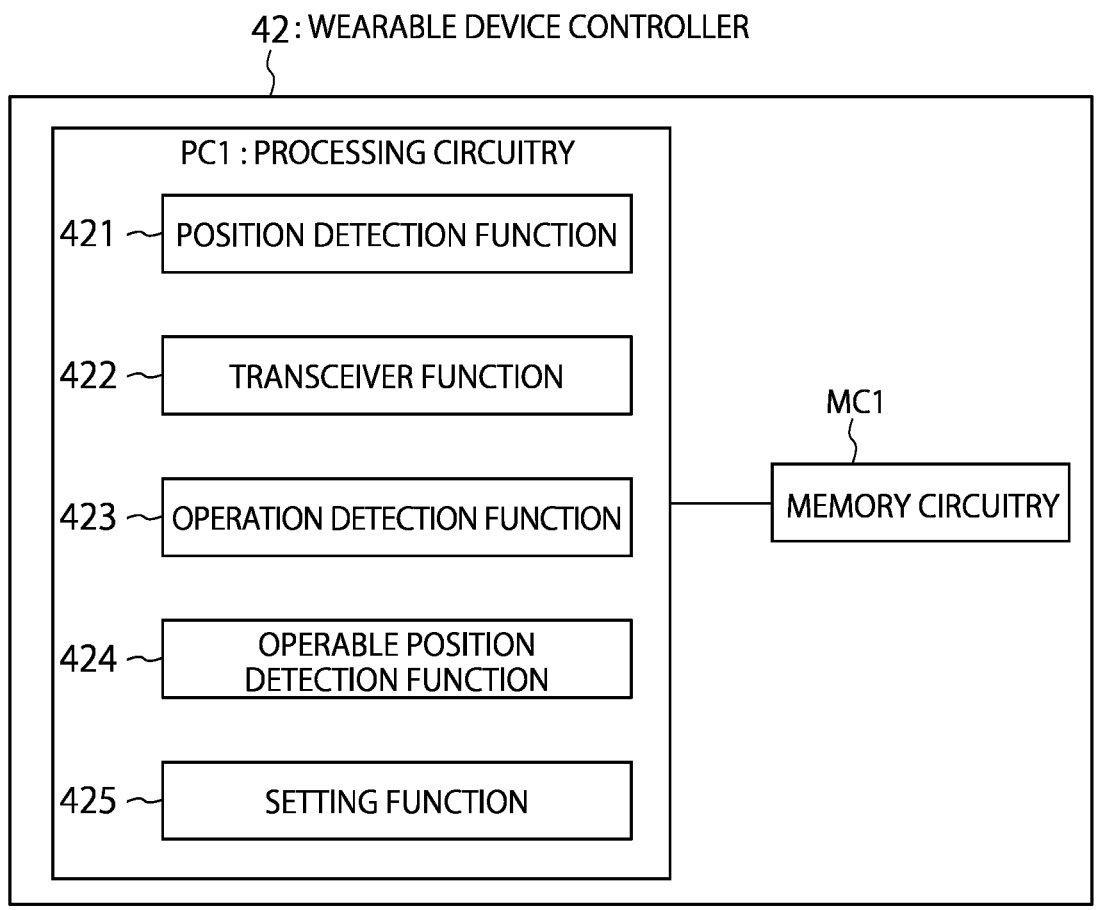
FIG. 6 is a block diagram functionally illustrating a processing configuration of a wearable device controller in the X-ray diagnosis system according to the first embodiment.

FIG. 6 is a block diagram illustrating a configuration of the wearable device controller 42. As shown in FIG. 6, the wearable device controller 42 according to the present embodiment has processing circuitry PC1 and memory circuitry MC1. The processing circuitry PC1 has a position detection function 421, a transceiver function 422, an operation detection function 423, an operable position detection function 424 and a setting function 425, as its processing functions. The position detection function 421 specifies position information and detects positions of the right and the left feet of the operator on the basis of a detection signal received from the position detection elements 50R and 50L in the wearable device 40 via the transceiver function 422. The transceiver function 422 transmits a control signal to the wearable device 40 and receives the detection signal concerning detection result for the operation from the wearable device 40.

The operation detection function 423 specifies and detects the operation by the operator on the basis of the detection signal received from the wearable device 40 via the transceiver function 422. The operable position detection function 424 judges whether the wearable device 40 is placed at a position at which the virtual switch is operable, and if the wearable device 40 is placed at such a position, vibrates the vibration devices 58R and 58L by transmitting the control signal to the wearable device 40 via the transceiver function 422. The setting function 425 sets the virtual foot switch 60 at a position settled relatively with respect to the operator and implements various settings on the virtual foot switch 60.

In the present embodiment in FIG. 6, each processing function that is executed respectively in the position detection function 421, the transceiver function 422, the operation detection function 423, the operable position detection function 424 and the setting function 425, are stored in the memory circuit MC1 in the form of programs that are executable by computer. The processing circuitry PC1 has a processor that reads out and executes the programs from the memory circuitry MC1 to implement functions corresponding to each of the programs. In other words, once the processing circuitry PC1 has read out each of the programs, the processing circuitry PC1 in the wearable device controller 42 has each of the functions shown in the processing circuitry PC1 in FIG. 6. In FIG. 6, the position detection function 421, the transceiver function 422, the operation detection function 423, the operable position detection function 424 and the setting function 425 are implemented with a single processor, however, these functions may also be implemented by combining a plurality of independent processors to constitute the processing circuitry PC1 in the wearable device controller 42 and by executing the programs with the processors.

Figure 7:
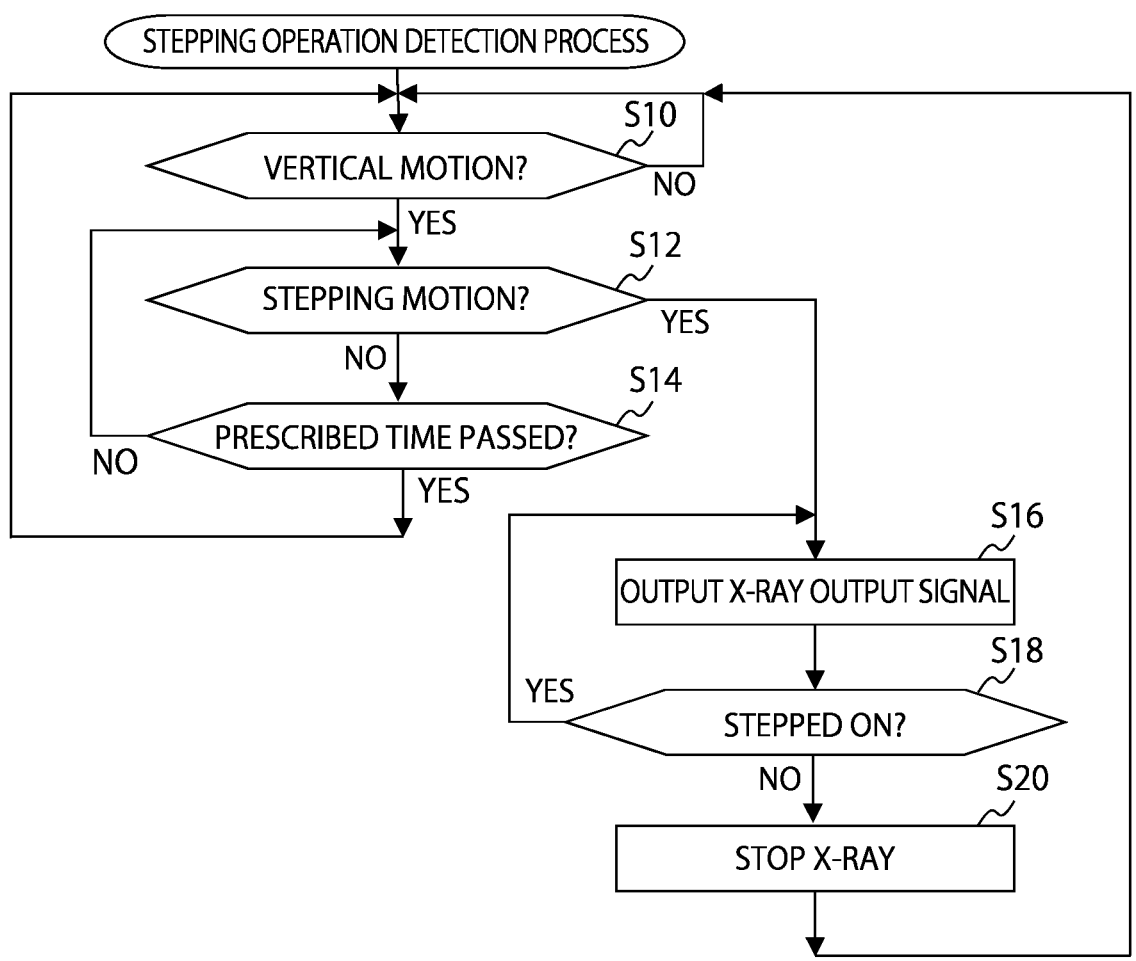
FIG. 7 is a flowchart illustrating an example of a stepping operation detection process executed by the wearable device controller in the X-ray diagnosis system according to the first embodiment.

FIG. 7 is a diagram illustrating an example of a stepping operation detection process to implement the operation detection function 423 in the wearable device controller 42 according to the present embodiment. FIG. 8A through FIG. 8C are diagrams illustrating examples of waveforms of various signals in the stepping operation detection process. More particularly, FIG. 8A shows a waveform of a detection signal of the acceleration sensor 54R, FIG. 8B shows a waveform of the detection signal of the pressure sensor 52R, and FIG. 8C shows a waveform of an X-ray output signal from the wearable device controller 42 to the system controller 18. In particular, FIG. 8C shows the X-ray output signal which is generated while the operator is stepping on the pedal PD2 of the virtual foot switch 60 with the right foot to irradiate the X-ray for the X-ray fluoroscopy.

As shown in FIG. 7, the wearable device controller 42 firstly analyzes the detection signal of the acceleration sensor 54R in the wearable device 40 and judges whether vertical motion is detected (STEP S10). As shown in FIG. 8A, when the stepping operation on a pedal of the virtual foot switch 60 is executed with the right foot or the dominant foot of the operator, the right foot firstly moves upwards to align with the pedal and then moves downwards at the pedal position. The acceleration sensor 54R detects the acceleration for the right foot to move upwards and then to move downwards. The wearable device controller 42 analyzes the detection signal of the acceleration sensor 54R and detects whether there is any vertical motion for the right foot. If there is no vertical motion (STEP S10: No), the wearable device controller 42 remains repeating the process of STEP S10.

It should be noted that, in judging whether there is any vertical motion for the right foot, time S may be taken into consideration. The time S stands for a period of time when the acceleration detection value by the detection signal of the acceleration sensor 54R is greater than the first threshold value. When the operator steps on a pedal of the virtual foot switch 60, the flight time between the right foot moving upwards and downwards is considered to be longer than the time for motions for other purposes. This flight time may be defined as the time S, which is greater than the first threshold value, and when the time S is equal to or longer than the prescribed time, the vertical motion of the right foot may be determined as executed.

Next, as shown in FIG. 7, the wearable device controller 42 then analyzes the detection signal of the pressure sensor 52R in the wearable device 40 and judges whether there is any stepping motion detected (STEP S12). As shown in FIG. 8B, when the stepping operation on a pedal of the virtual foot switch 60 is executed with the right foot i.e. the dominant foot of the operator, pressure detected by the pressure sensor 52R at the pedal position becomes great enough that the pedal is being stepped on, and eventually turns smaller. The wearable device controller 42 analyzes the detection signal of the pressure sensor 52R and judges whether the pedal is being stepped on by being applied pressure equal to or greater than the second threshold value with the right foot i.e. the dominant foot.

If there is no stepping motion detected (STEP S12: No), the wearable device controller 42 judges whether the prescribed time T has passed after the acceleration by the detection signal of the acceleration sensor 54R becomes greater than the first threshold value (STEP S14). When the operator executes the stepping motion on the pedal, a series of motions is considered to start with the right foot moving upwards and end with the actual stepping in. Accordingly, if a certain period of time has passed since the right foot moving upwards, it is not considered to be stepping motion on the pedal. Thus, in the present embodiment, if the prescribed time T passes after the acceleration becomes greater than the first threshold value (STEP S14: Yes), the wearable device controller 42 judges that the motion is not stepping motion on the pedal and returns to the above-mentioned STEP S10.

On the other hand, if the prescribed time T has not passed after the acceleration becomes greater than the first threshold value (STEP S14: No), the wearable device controller 42 returns to the above-mentioned STEP S12 to analyze the detection signal by the pressure sensor 52R of the wearable device 40, and continuously judges whether there is any stepping motion detected. If stepping motion is detected before the prescribed time T has passed (STEP S12: Yes), the wearable device controller 42 outputs the X-ray output signal to the system controller 18 (STEP S16). On the basis of this X-ray output signal, the system controller 18 irradiates X-ray. For example, if the right foot of the operator is placed on the pedal PD2 position of the virtual foot switch 60, the system controller 18 irradiates X-ray used for X-ray fluoroscopy to obtain simultaneous an X-ray fluoroscopic image. In the present embodiment, the X-ray used for X-ray fluoroscopy is irradiated while the operator is stepping on the pedal PD2 with the right foot.

The wearable device controller 42 then judges whether the pedal is kept stepped on (STEP S18), and if the pedal is kept stepped on (STEP S18: Yes), the wearable device controller 42 returns to STEP S16 to continuously output the X-ray output signal. On the other hand, if the wearable device controller 42 judges that the pedal is no longer kept stepped on (STEP S18: No), the wearable device controller 42 stops outputting the X-ray output signal (STEP S20). Consequently, the system controller 18 stops irradiating the X-ray. The wearable device controller 42 then returns to the above-mentioned process in STEP S10.

As shown in FIG. 8C, while a pressure of the detection signal of the pressure sensor 52R is greater than the second threshold value, the X-ray output signal reaches a high state and is output to the system controller 18. This means that X-ray is irradiated while the operator is stepping on at the pedal position of the virtual foot switch 60 with the right foot. The operator, therefore, is able to operate the pedal PD2 as if there were a physical foot switch even though there is not.

Incidentally, if the operator places the right foot on the pedal PD1 position of the virtual foot switch 60 and steps on the pedal PD1 with the right foot, X-ray photograph is executed. In other words, if the pedal PD1 is stepped on, the system controller 18 irradiates X-ray for X-ray photograph to obtain an X-ray image on the basis of the X-ray detection signal, although this X-ray irradiation is only one time regardless of how long the pedal PD1 is being stepped on.

Moreover, in order to avoid unnecessary exposure to the subject, or to avoid malfunction, the wearable device controller 42 may stop outputting the X-ray output signal if a vertical motion of the right foot is detected by the detection signal of the acceleration sensor 54R, even when pressure detected by the pressure sensor 52R is greater than the second threshold value.

Figure 8:
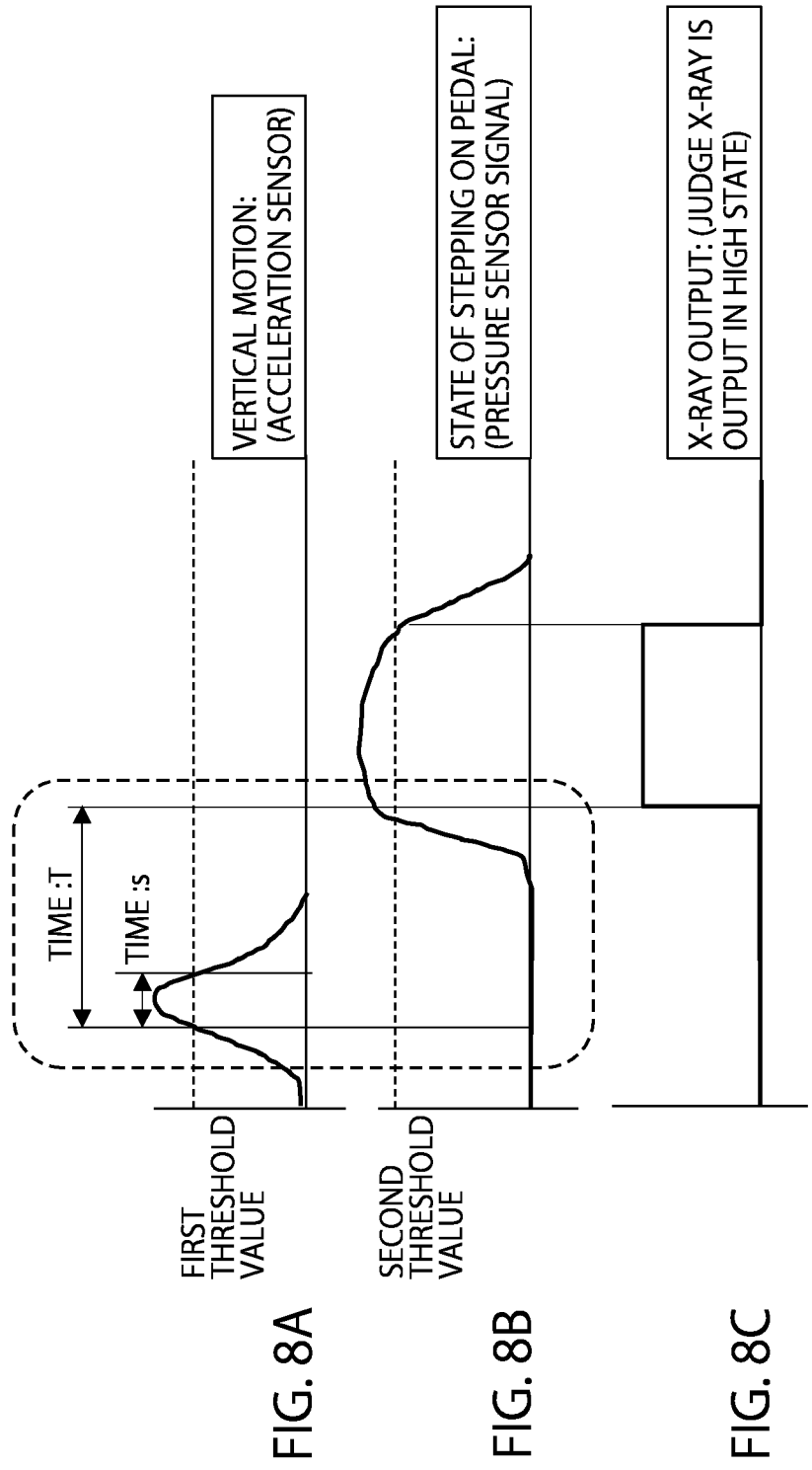
FIG. 8A is a diagram illustrating an example of a waveform of a detection signal of an acceleration sensor in the stepping operation detection process in FIG. 7.
FIG. 8B is a diagram illustrating an example of a waveform of the detection signal of a pressure sensor in the stepping operation detection process in FIG. 7.
FIG. 8C is a diagram illustrating an example of a waveform of X-ray output signal from the wearable device controller to a system controller in the stepping operation detection process in FIG. 7.

In order to avoid unintentional operation on the virtual foot switch, a function for switching the virtual foot switch 60 between an activation state and a deactivation state may also be additionally provided. In this case, the virtual foot switch 60 may alternately be in the activation state and the deactivation state, for example when the right or left foot moves in a certain way. For example, the virtual foot switch 60 may alternately be in the activation state and the deactivation state when the stepping motion shown in FIG. 8 is detected by the acceleration sensor 54L and the pressure sensor 52L of the left foot or the pivot foot. Furthermore, for example, the virtual foot switch 60 may alternately be in the activation state and the deactivation state when a plurality of tapping motions are detected by the acceleration sensor 54L and the pressure sensor 52L of the left foot. These activating and deactivating motions may be performed with the right and/or left foot.

The function of the virtual foot switch 60 may also be deactivated when the operator with the wearable device 40 leaves the bed 28 for the prescribed distance or further. This prevents, for example, misoperation on the virtual foot switch 60 in consequence of walking motion of the operator. In particular, for example, this prevents misoperation, which happens when the operator is leaving the examination room temporarily.

Figure 9:
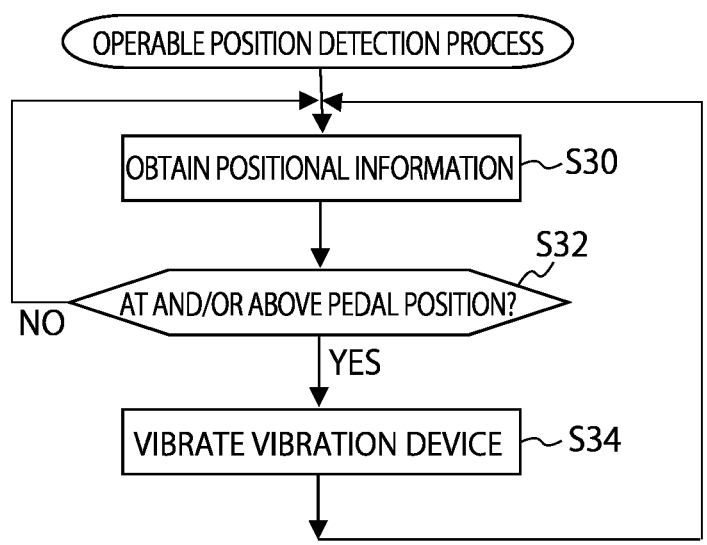
FIG. 9 is a flowchart illustrating an example of an operable position detection process executed by the wearable device controller in the X-ray diagnosis system according to the first embodiment.

FIG. 9 is a diagram illustrating an example of an operable position detection process for achieving the operable position detection function 424 in the wearable device controller 42 according to the present embodiment. In this operable position detection process, the wearable device controller 42 firstly obtains positional information for the wearable device 40 (STEP S30). In particular, the wearable device controller 42 obtains two pieces of positional information respectively from the position detection element 50R in the right device 40R and the position detection element 50L in the left device 40L.

The wearable device controller 42 then specifies a relative position of the right foot for operating on the basis of the position of the left foot i.e. the pivot foot, and judges whether the relative position is at any one of the pedals PD1, PD2 and PD3 of the virtual foot switch 60 (STEP S32). In other words, the wearable device controller 42 judges whether the relative position of the right foot is at the pedal PD1, at the pedal PD2, or at the pedal PD3. If the relative position of the right foot is neither at the pedals PD1, PD2 nor PD3 (STEP S32: No), the wearable device controller 42 returns to the above-mentioned STEP S30.

On the other hand, if the relative position of the right foot on the basis of the left foot of the pivot foot is at a pedal position at which any one of the pedals PD1, PD2 and PD3 of the virtual foot switch 60 is operable and/or if the relative position of the right foot is above any one of the pedals PD1, PD2 and PD3 (STEP S32: Yes), the wearable device controller 42 vibrates the vibration device 58R for the right foot (STEP S34). In particular, the wearable device controller 42 transmits control signal for vibrating the vibration device 58R to the signal transceiver 56R via the transceiver function 422, and vibrates the vibration device 58R provided in the right device 40R. This allows the operator to be notified that the right foot is at and/or above any one of the pedals PD1, PD2 and PD3. The wearable device controller 42 then returns the above-mentioned STEP S30.

In STEP S34, a period of time for vibrating the vibration device 58R is optional. The vibration device 58R is vibrated for the prescribed period of time, such as three or five seconds. Further, in addition to the vibration device 58R for the right foot, the vibration device 58L for the left foot may also be vibrated. Vibrating the vibration device 58L in the left device 40L for the pivot foot further ensures to notify the operator that the right foot for operating pedals is at and/or above any one of the pedals PD1, PD2 and PD3.

The vibration of the vibration device 58R may also have various types depending on each pedal so that the operator can identify which pedal out of the pedals PD1, PD2 and PD3 the right foot for operating is at. In other words, having various types of vibration depending on each pedal allows the operator to identify each pedal on the basis of the vibration. For example, the vibration device 58R may vibrate for one second when the right foot is above the pedal PD1, for three seconds when the right foot is above the pedal PD2, and for five seconds when the right foot is above the pedal PD3. Alternatively, the vibration device 58R may vibrate continuously when the right foot is at and/or above the pedal PD1, intermittently with short intervals when the right foot is at and/or above the pedal PD2, and intermittently with long intervals when the right foot is at and/or above the pedal PD3.

The operator may also be notified by sound instead of the vibration of the vibration devices 58R and 58L. For example, a beep may be generated by the wearable device controller 42 or the wearable device 40 when the right foot is above any one of the pedals PD1, PD2 and PD3. In this case, the beep may have various types depending on each pedal so that the operator can identify which pedal the right foot is at.

Further, instead of, or in addition to vibrating the vibration devices 58R and 58L, the display monitor 36 may also notify that the right foot is at an operable position of the pedals. For example, the display monitor 36 may display letters that indicates "above pedal" when the right foot is above any one of the pedals PD1, PD2 and PD3. In this case, the letters on the display monitor 36 may vary depending on each pedal so that the operator can identify which pedal the right foot is at. For example, the display monitor 36 may display "the first pedal" when the right foot is at and/or above the pedal PD1, "the second pedal" when right foot is at and/or above the pedal PD2, and "the third pedal" when the right foot is at and/or above the pedal PD3.

Figure 10:
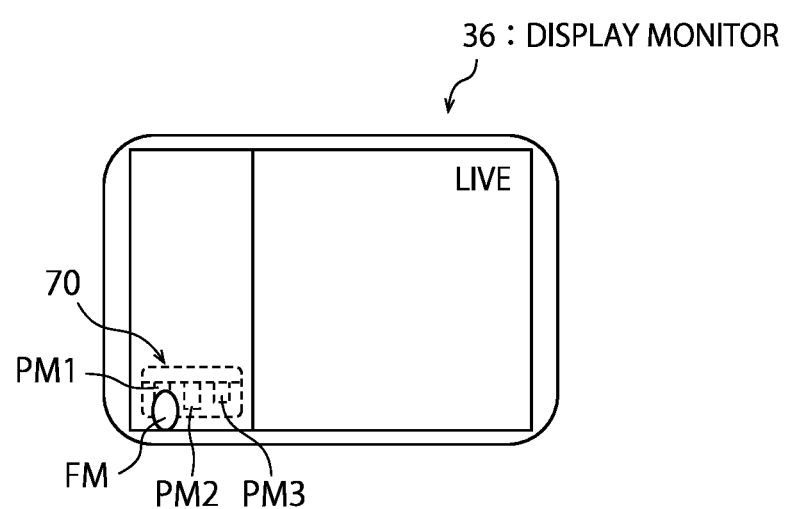
FIG. 10 is a diagram illustrating an example of an operation image of a visually detectable virtual foot switch displayed on a display monitor in the X-ray diagnosis system according to the first embodiment.

Further, instead of, or in addition to vibrating the above-mentioned vibration devices 58R and 58L, the display monitor 36 may visually display the position of the right foot in the virtual foot switch 60 as an auxiliary image shown in FIG. 10. In the example of the display monitor 36 shown in FIG. 10, the display monitor 36 displays a foot switch mark 70 as an auxiliary image, which is a simplified image of the virtual foot switch 60, at the bottom-left corner of the display. This foot switch mark 70 includes a pedal mark PM1 corresponding to the pedal PD1, a pedal mark PM2 corresponding to the pedal PD2, and a pedal mark PM3 corresponding to the pedal PD3. So as to overlap these pedal marks PM1, PM2 and PM3, the display monitor 36 also displays a foot mark FM corresponding to the right foot of the operator.

For example, the display monitor 36 displays the foot mark FM overlapping the pedal mark PM1 when the right foot is at and/or above the pedal PD1 of the virtual foot switch 60. Similarly, the display monitor 36 displays the foot mark FM overlapping the pedal mark PM2 when the right foot is at and/or above the pedal PD2 of the virtual foot switch 60. The display monitor 36 displays the foot mark FM overlapping the pedal mark PM3 when the right foot is at and/or above the pedal PD3 of the virtual foot switch 60.

Displaying such foot switch mark 70 as an auxiliary image on the display monitor 36 allows the operator to identify whether the right foot for operating is at a position which allows the operator steps on the pedal PD1, at a position which allows the operator steps on the pedal PD2, or at a position which allows the operator steps on the pedal PD3.

Figure 11:
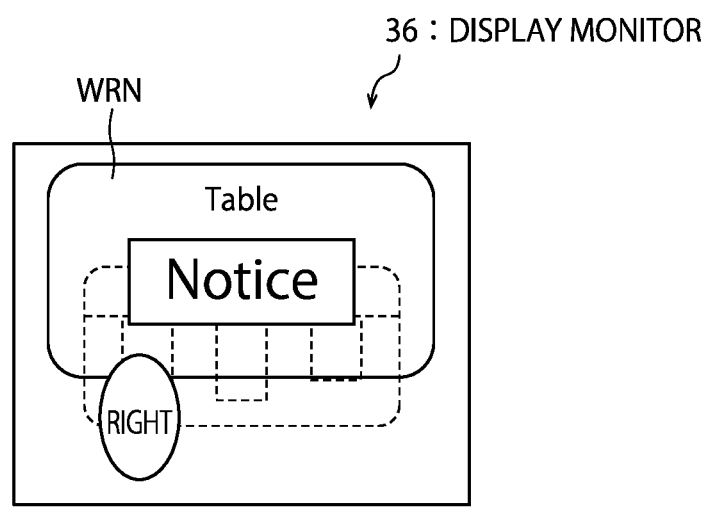
FIG. 11 is a diagram illustrating an example of a warning given to the operator, which is displayed on the display monitor in the X-ray diagnosis system according to the first embodiment.

If the display monitor 36 is to be used in this manner, the display monitor 36 may display warning information WRN as shown in FIG. 11 if the position of the virtual foot switch 60 interferes with other peripheral apparatus. The reason behind this is the position of the virtual foot switch 60 may overlap the positions of the bed 28, the holding device 20 or other peripheral apparatus such as an ultrasonic device and anesthetization equipment, resulting in interfering with them. In this case, the display monitor 36 displays the warning information WRN to notify the operator that the virtual foot switch 60 is not properly operable. This warning is not necessarily a form of the letters displayed on the display monitor 36, but may also be warning sound for example, for notifying the operator.

After the warning, the setting function 425 of the wearable device controller 42 may reset the virtual foot switch 60 at a pre-set default position so that it does not interfere. Alternatively, the wearable device controller 42 may temporarily deactivate the function of the virtual foot switch 60 and re-activate it if the virtual foot switch 60 is no longer interfering. Further, in order to re-activate the temporarily deactivated function of the virtual foot switch 60, the wearable device controller 42 may require the operator to input a certain instruction for the sake of safety.

Further, the quantity, the size and the layout of the pedals of the virtual foot switch 60 may optionally be designed differently in accordance with the X-ray diagnosis apparatus 1. These elements of the foot switch 60 may also have customizable settings for each operator. FIG. 12 is a diagram illustrating an example of a configuration of a user information table TB1 stored by a setting function 425 of the wearable device controller 42 so that the settings of the foot switch 60 can be changeable for each operator.

As shown in FIG. 12, the wearable device controller 42 holds the user information table TB1 for each operator. The user information table TB1 holds user ID to identify the operator. Furthermore, the user information table TB1 also holds information on the quantity, the size and the layout of the pedals, which is associated with the user ID.

The quantity of the pedals indicates the number of the pedals, such as three or four. The size of the pedals indicates information specifying the size of the pedals, such as large, medium and small. The layout of the pedals indicates layout information, such as a pattern A with narrow spacing between the pedals, a pattern B with wider spacing between the pedals and a pattern C with even wider spacing between the pedals. For example, the setting information may be input and set beforehand through the operating the wearable device controller 42.

Alternatively, the wearable device 40 and the setting function 425 of the wearable device controller 42 cooperate so that the operator may set these settings by operating the wearable device 40. For example, the wearable device controller 42 displays instructions saying "Step on at the first pedal position with your right foot" on the display monitor 36, and the first pedal position is set at a position at which the operator stepped on with the right foot in accordance with the instructions. Positions for all the pedals are set by repeating this procedure for the rest of the pedals.

When operating the X-ray diagnosis apparatus 1, the operator invokes the pre-set foot switch 60 by inputting the personal user ID to the wearable device controller 42. Alternatively, the settings for the foot switch 60 may be automatically invoked on the basis of the name of the operator, which is included in information on examination executed with the X-ray diagnosis apparatus 1 and is obtained by the X-ray diagnosis system 2.

Further, in the X-ray diagnosis system 2 according to the present embodiment, the distance and the direction from the pivot foot to the virtual foot switch 60 may also optionally be adjusted for each operator. For example, this is implemented as the setting function 425 by executing a pedal position adjustment process shown in FIG. 13 using the wearable device controller 42. FIG. 14 shows an example of the operation made by the operator in the pedal position adjustment process.

Figure 13:
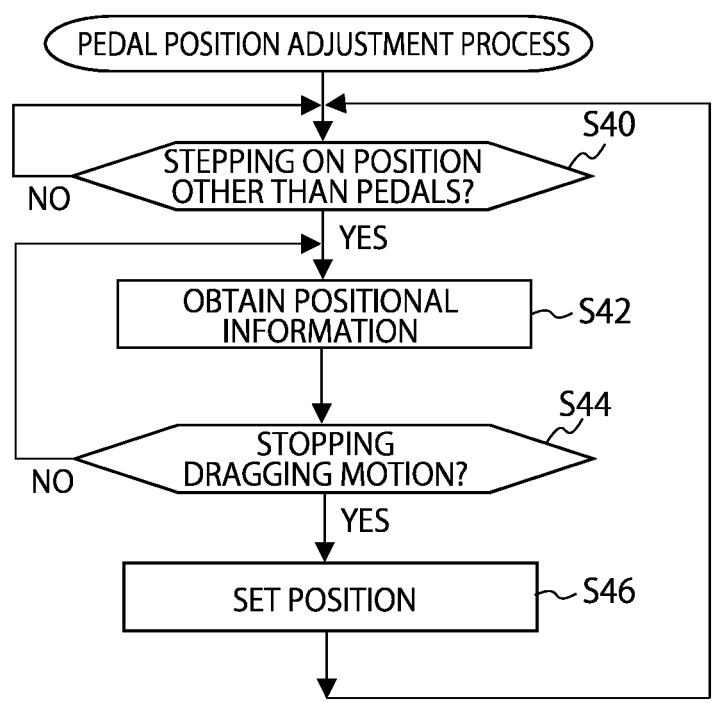
FIG. 13 is a flowchart illustrating an example of a pedal position adjustment process executed by the wearable device controller in the X-ray diagnosis system according to the first embodiment.
Figure 14:
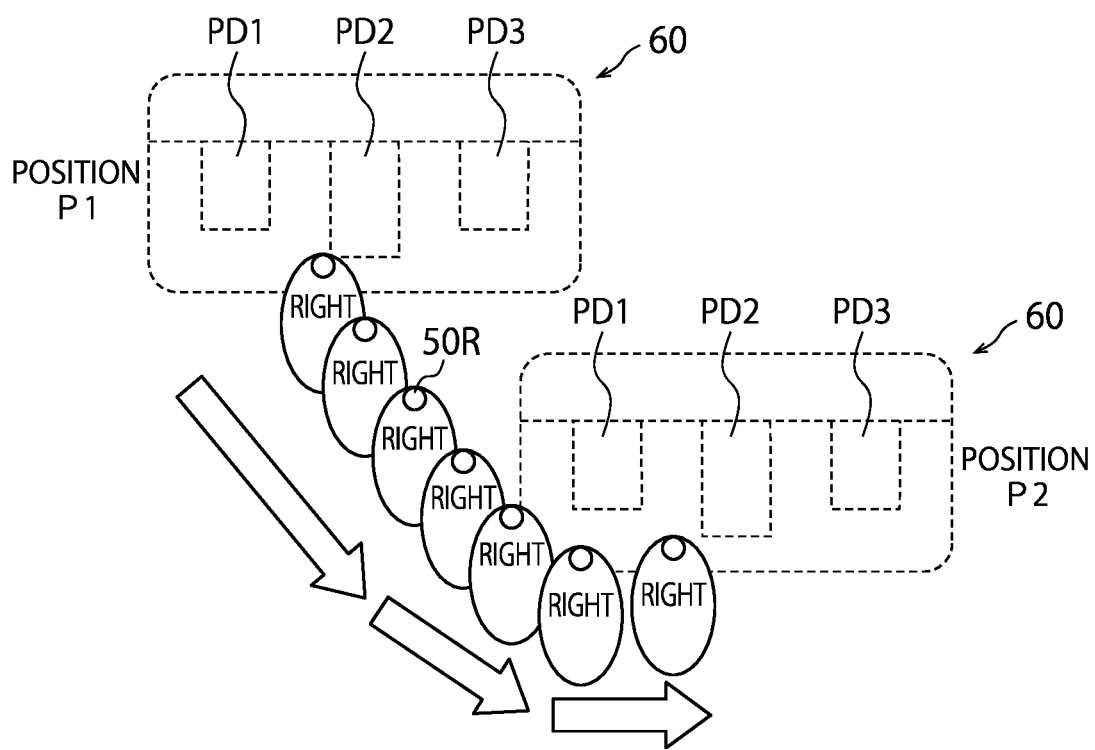
FIG. 14 is a diagram illustrating an example of a motion when the operator adjusts a position of the virtual foot switch in the pedal position adjustment process in FIG. 13.

As shown in FIG. 13, in the pedal position adjustment process, the wearable device controller 42 firstly judges whether the right foot of the operator steps on a position other than the pedals of the virtual foot switch 60 (STEP S40). For example, as shown in FIG. 14, the wearable device controller 42 judges that the operator steps on a position other than the pedals of the virtual foot switch 60 if the operator steps on the lower edge of the virtual foot switch 60 by the right foot.

If the wearable device controller 42 judges that the right foot of the operator steps on a position other than the pedals of the virtual foot switch 60 (STEP S40: Yes), the wearable device controller 42 obtains positional information of the right foot of the operator (STEP S42). More specifically, the wearable device controller 42 obtains the position information of the right foot in dragging motion because the operator drags the virtual foot switch 60 to a desired position with the right foot.

The wearable device controller 42 continues to obtain the position information of the right foot until the dragging motion stops (STEP S44: No). The wearable device controller 42 judges that the dragging motion is ongoing, for example, if a detection result of the pressure sensor 52R of the right foot of the operator indicates a pressure equal to or greater than the prescribed threshold value while a detection result of the position detection element 50R indicates that the motion of the right foot is ongoing. Conversely, the wearable device controller 42 judges that the dragging motion stopped, for example, if the detection result of the pressure sensor 52R of the right foot of the operator indicates a pressure less than the prescribed threshold value, or if the detection result of the position detection element 50R indicates that the motion of the right foot stopped.

If the dragging motion with the right foot of the operator stops (STEP S44: Yes), the wearable device controller 42 sets the virtual foot switch 60 at a position at which the operator stopped the dragging motion with the right foot (STEP S46). FIG. 14 shows an example of the virtual foot switch 60 moving from a position P1 to a position P2 in consequence of dragging the virtual foot switch 60 with the right foot of the operator. Under the circumstances shown in FIG. 14, the left foot of the pivot foot remains the same position and does not move. Thus, the relative position of the foot switch 60 relatively moves with respect to the left foot of the pivot foot. For example, the position information set in this manner is stored in the setting function 425 of the wearable device controller 42. The wearable device controller 42 then returns to the above-mentioned STEP S40 to continue the pedal position adjustment process.

As explained above, the X-ray diagnosis system 2 according to the present embodiment eliminates the need for looking for a physical foot switch to irradiate X-ray by setting the virtual foot switch at a position settled relatively with respect to the operator, who operates the X-ray diagnosis apparatus 1. Consequently, the operator is no longer required to look at a physical foot switch and is relieved from a burden of looking away from the display monitor 36 every time the operator operates the X-ray diagnosis apparatus 1. This contributes to relieving the stress of the operator during procedures and improving efficiency of the procedures. As a result, the procedures are able to be completed in a shorter period of time.

Second Embodiment

When the operator steps on a pedal of the virtual foot switch 60, in the X-ray diagnosis system 2 according to the above-mentioned first embodiment, the operator requires the whole right foot to move in a horizontal direction to reach a pedal to be stepped on. On the other hand, in the X-ray diagnosis system 2 according to a second embodiment, the operator requires the right foot to move pivotally around the heel to reach a pedal to be stepped on because the pedals of the virtual foot switch 60 are arranged as a fan shape. The detailed explanation different form the above-mentioned first embodiment will be made below.

Figure 15:
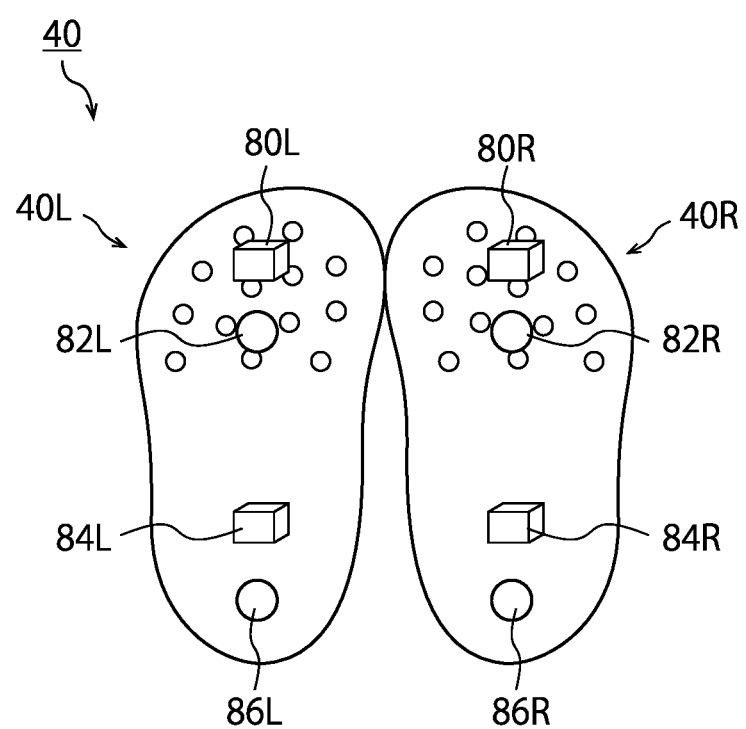
FIG. 15 is a diagram illustrating an example of a configuration of a wearable device according to a second embodiment.

FIG. 15 is a diagram illustrating a configuration of the wearable device 40 in the X-ray diagnosis system 2 according to the present embodiment. As shown in FIG. 15, the wearable device 40 in the present embodiment also has a right device 40R to be worn on the right foot and a left device 40L to be worn on the left foot.

In the present embodiment, however, the right device 40R and the left device 40L respectively have first acceleration sensors 80R and 80L as well as first pressure sensors 82R and 82L in the vicinities of the thenar eminences. In the present embodiment, the right device 40R and the left device 40L further respectively have second acceleration sensors 84R and 84L as well as second pressure sensors 86R and 86L in the vicinities of the heel portions. The function of the first acceleration sensors 80R and 80L as well as the second acceleration sensors 84R and 84L is the same as the function of the acceleration sensors 54R and 54L in the first embodiment. The function of the first pressure sensors 82R and 82L as well as the second pressure sensors 86R and 86L is the same as the function of the pressure sensors 52R and 52L in the first embodiment.

In the present embodiment, the first acceleration sensors 80R and 80L, the first pressure sensors 82R and 82L, the second acceleration sensors 84R and 84L, as well as the second pressure sensors 86R and 86L constitute a detector for detecting operation on the virtual switch by the operator.

It should be noted that the wearable device 40 in the present embodiment also has the signal transceivers 56R and 56L as well as the vibration devices 58R and 58L in the first embodiment, although those elements and devices are omitted and not shown in FIG. 15.

Figure 16:
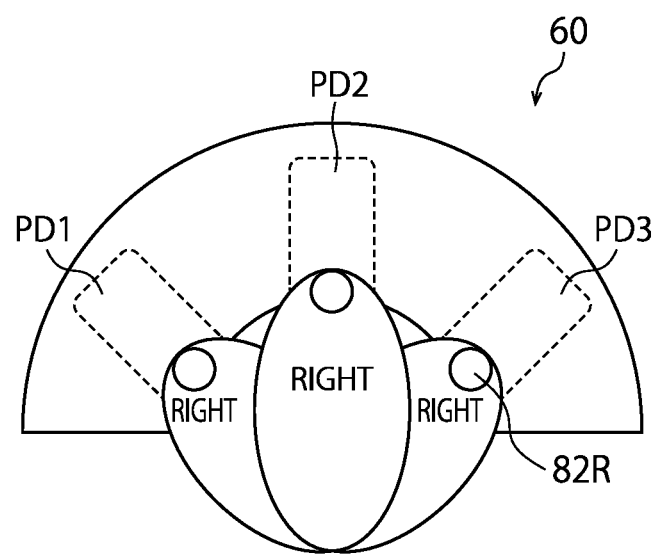
FIG. 16 is a diagram illustrating an example of a motion when an operator operates a virtual foot switch in an X-ray diagnosis system according to the second embodiment.

FIG. 16 is a diagram illustrating an example of a virtual foot switch 60 set at a position settled relatively with respect to the operator in the X-ray diagnosis system 2 in the present embodiment. The virtual foot switch 60 in the present embodiment is also set in the prescribed direction from the prescribed distance in accordance with the left foot i.e. the pivot foot by the wearable device controller 42. However, in the virtual foot switch 60 according to the present embodiment, the pedals PD1, PD2 and PD3 are set as a fan shape. This means that the operator moves the toe portion of the right foot to the right and left directions pivotally around the heel portion to choose a pedal to step on.

To step on the pedal PD1, for example, the operator places the toe portion of the right foot at the pedal PD1 position by moving the toe portion to the left direction pivotally around the heel portion of the right foot. The operator can then step on the pedal PD1 of the virtual foot switch 60 by putting a pressure with the toe portion of the right foot. Whether the stepping on with the toe portion of the right foot is executed is judged by a pressure value detected by the first pressure sensor 82R.

For example, it is judged that the right foot is moving pivotally, if a detection result of the first acceleration sensor 80R indicates that the prescribed acceleration is detected while a detection result of the second acceleration sensor 84R indicates that no acceleration is detected at the same time that a detection result of the second pressure sensor 86R indicates that the prescribed pressure is detected.

As explained above, in the X-ray diagnosis system 2 according to the present embodiment, the pedals of the virtual foot switch 60 may be set as a fan shape. This allows the operator of the X-ray diagnosis apparatus 1 to move the right foot for operating the pedals pivotally around the heel portion to choose one of the pedals of the virtual foot switch 60 to step on in order to operate the X-ray diagnosis apparatus 1. This also means a pedal layout of the virtual foot switch 60 can be optionally selected in accordance with the type of the X-ray diagnosis apparatus 1 or with the personal preference of the operator.

Third Embodiment

In the X-ray diagnosis system 2 according to the above-mentioned first and second embodiments, the virtual foot switch 60 is provided with the plurality of the pedals PD1, PD2 and PD3 and specific operation function assigned to the pedals PD1, PD2 and PD3, respectively, however, the operation functions of the pedal of the virtual foot switch 60 are not necessarily fixed. As such, in the X-ray diagnosis system 2 according to a third embodiment, a plurality of operation functions are assigned to a single pedal and the operation functions of the pedal can be shifted by shifting operation.

Figure 17:
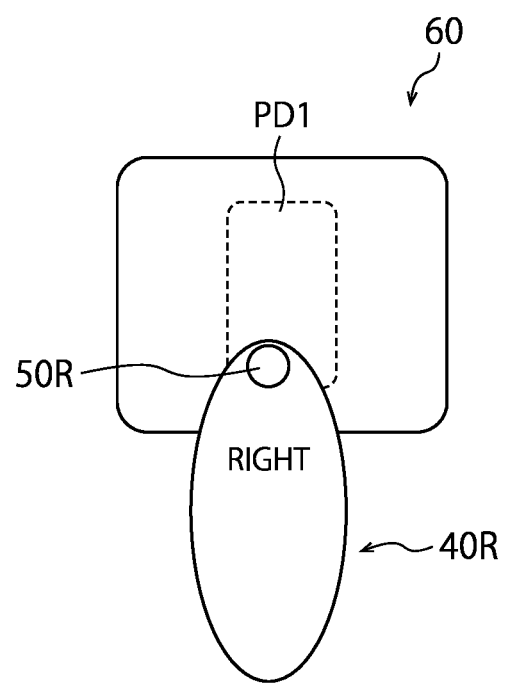
FIG. 17 is a diagram illustrating an example of a layout of a virtual foot switch in an X-ray diagnosis system according to the third embodiment.

FIG. 17 is a diagram illustrating an example of a layout of the virtual foot switch 60 in the X-ray diagnosis system 2 according to the present embodiment, corresponding to FIG. 5 in the above-mentioned first embodiment. As shown in FIG. 17, the virtual foot switch 60 according to the present embodiment is set with a single pedal PD1. The operator uses the single pedal PD1 by shifting the operation functions thereof.

There are various possible types of the function shifting operation to shift the functions of the pedal PD1. The wearable device controller 42 may judge that the function shifting operation for the functions of the foot switch 60 is executed, for example, if the operator executes a tapping motion with the right foot, if the operator executes a dragging operation on the foot switch 60 with the right foot, or if the operator executes a flicking operation on the foot switch 60.

In the present embodiment, for example, the virtual foot switch 60 has both functions for a pedal for executing X-ray photograph to obtain X-ray image, and a pedal for executing X-ray fluoroscopy to obtain an X-ray fluoroscopic image in real time. These two functions are alternately shifted when the operator executes the function shifting operation. More specifically, in the case when the pedal PD1 is serving as a pedal for executing X-ray photograph to obtain X-ray image, the pedal PD1 will serve as a pedal for executing X-ray fluoroscopy to obtain the X-ray fluoroscopic image in real time after the function shifting operation by the operator. Conversely, in the case when the pedal PD1 is serving as a pedal for executing X-ray fluoroscopy to obtain the X-ray fluoroscopic image in real time, the pedal PD1 will serve as a pedal for executing X-ray photograph to obtain X-ray image after the function shifting operation by the operator.

Figure 18:
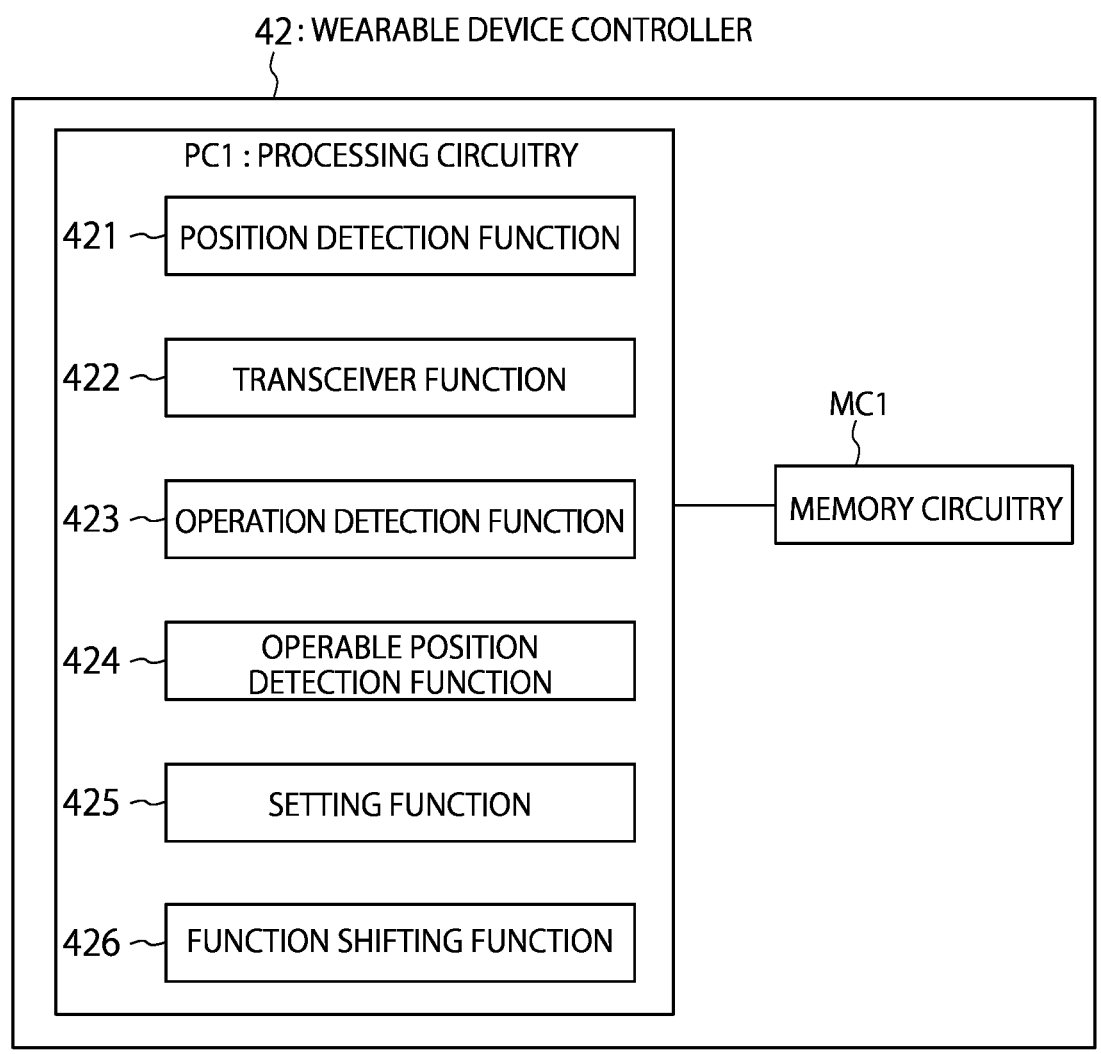
FIG. 18 is a block diagram illustrating a configuration of a wearable device controller in the X-ray diagnosis system according to the third embodiment.

FIG. 18 is a block diagram illustrating a configuration of the wearable device controller 42, corresponding to FIG. 6 in the above-mentioned first embodiment. As shown in FIG. 18, the processing circuitry PC1 of the wearable device controller 42 according to the present embodiment has a function shifting function 426 in addition to the function of the processing circuitry PC1 according to the above-mentioned first embodiment. This function shifting function 426 implements the above-mentioned function shifting operation by the operator. More specifically, the function shifting function 426 of the processing circuitry PC1 detects the function shifting operation by the operator and shifts the functions of the pedal PD1 of the foot switch 60.

Similarly to the above-mentioned first embodiment, this function shifting function 426 is also stored in the memory circuitry MC1 in the form of a program that is executable by computer. The processing circuitry PC1 of the wearable device controller 42 implements the function shifting function 426 shown in the processing circuitry PC1 in FIG. 18 after reading out the program. It should be noted that the processing circuitry PC1 may implement the function shifting function 426 with a single processor, or a plurality of independent processors may be combined to have the processing circuitry PC1 of the wearable device controller 42 and execute the program to implement the function shifting function 426.

Figure 19:
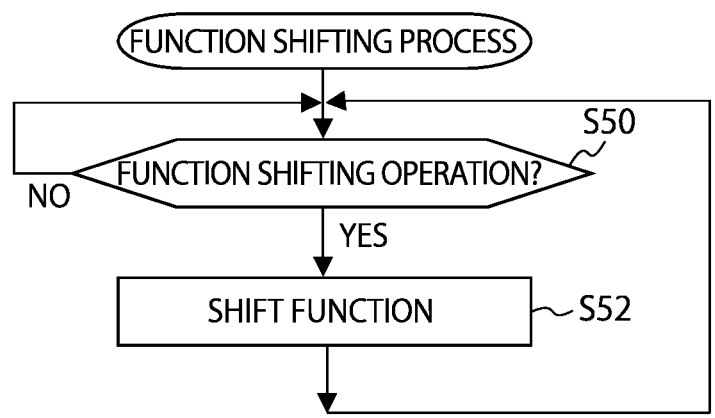
FIG. 19 is a diagram illustrating an example of a function shifting process to implement a function shifting function in the wearable device controller according to the third embodiment.

FIG. 19 is a diagram illustrating an example of a function shifting process to implement the function shifting function 426 in the wearable device controller 42 according to the present embodiment. As shown in FIG. 19, the wearable device controller 42 firstly judges whether the above-mentioned function shifting operation by the operator is detected (STEP S50). If the function shifting operation by the operator is not executed (STEP S50: No), the wearable device controller 42 remains repeating the STEP S50.

On the other hand, if the wearable device controller 42 detects the function shifting operation by the operator (STEP S50: Yes), the wearable device controller 42 shifts the functions of the pedal PD1 of the virtual foot switch 60 (STEP S52). In the present embodiment, the wearable device controller 42 alternately shifts two functions for the pedal PD1. One is for executing X-ray photograph to obtain X-ray image, and the other one is for executing X-ray fluoroscopy to obtain simultaneous X-ray fluoroscopic image. The wearable device controller 42 then returns to the above-mentioned STEP S50.

It should be noted that the present embodiment has been described with an example, which two operation functions are assigned to the single pedal PD1, however, the quantity of the operation functions assigned to the single pedal PD1 is not limited to two, although it needs to be plural. For example, if three operation functions are assigned to the single pedal PD1, these three operation functions should be shifted in order, every time the operator executes the function shifting operation.

Further, the quantity of the pedal of the virtual foot switch 60 is also not limited to one. A plurality of pedals may be provided, and a plurality of operation functions may be assigned to each of the pedals. For example, operation functions 1 and 2 may be assigned to the pedal PD1, and operation functions 3 and 4 may be assigned to the pedal PD2.

As explained above, the X-ray diagnosis system 2 according to the present embodiment contributes to reducing the quantity of the pedal of the virtual foot switch 60 as much as possible, by assigning a plurality of operation functions to the single pedal PD1 and shifting those functions by the function shifting operation by the operator. This also leads to downsizing the virtual foot switch 60 and prevents the foot switch 60 from interfering with the X-ray diagnosis apparatus 1.

The above-mentioned each embodiment has been described with an example of the foot switch 60, which is set at a position settled relatively with respect to the operator and operated by the foot of the operator, however, the present embodiment is not limited to this example and is applicable to any kind of switch of the X-ray diagnosis apparatus 1 operated by the operator. For example, as a virtual switch, a switch operated by a hand of the operator for the X-ray diagnosis apparatus 1 may also be virtually set. In this case, for example, the virtual switch may be set at a position settled relatively with respect to the head of the operator and a glove may be worn on the hand of the operator as the wearable device 40.

The above-mentioned each embodiment has been described with an example, which the wearable device 40 worn on the operator is an operation device, however, the operation device is not limited to a device that is wearable. For example, the operation on the virtual foot switch 60 may be detected by filming motion of the operator with a capturing camera and analyzing the captured image to specify the motion of both right and left feet of the operator. In this case, the capturing camera and an analysis device for the captured image serve as the operation device, instead of the above-mentioned wearable device 40.

In this case, the operator may be notified of the operational state by sound and/or light. That is, in the above-mentioned examples in which the operation device is the wearable device 40, the notification of the operational state such as a notification for notifying that the body portion of the operator is at and/or above a pedal position at which the pedal of the foot switch 60 is operable, is performed by vibrating the vibration devices 58L and 58R. However, when the operation device is the capturing camera and the analysis device for the captured image, the operator may be notified by the sound and/or the light generated by the operation device.

Further, the above-mentioned each embodiment has been described with an example in which the wearable device 40 detects the operational state of the operator, however, the present embodiment is not limited to this example. The functions of the wearable device 40 may be assigned to a plurality of devices. For example, the stepping operation motion and the operational state may be detected by a camera, and the pedal position may be detected by the wearable device 40.

The above-mentioned explanation has been described with an example, which the "processor" of the wearable device controller 42 reads out a program corresponding to each processing function from memory circuitry and executes it, however, the present embodiment is not limited to this example. The term "processor" denotes circuitry including Central Processing Unit (CPU), Graphics Processing Unit (GPU), Application Specific Integrated Circuit (ASIC), Programmable Logic Device such as Simple Programmable Logic Device (SPLD), Complex Programmable Logic Device (CPLD) and Field Programmable Gate Array (FPGA). When the processor is CPU for example, the processor implements each processing function by reading out and executing a program stored in the memory circuitry. On the other hand, when the processor is ASIC for example, the processing function is incorporated directly in circuitry of the processor as logical circuitry, and no program is stored in the memory circuitry. Each processor of the present embodiment may implement the processing function, not only when each processor has a single circuit, but also when a plurality of independent circuits is combined into one processor. Further, each processor may also implement the processing function by integrating a plurality of components in FIG. 1 into one processor. This also applies to the system controller 18. Alternately, the wearable device controller 42 and the system controller 18 may be considered as the "processing circuitry", being integrated into one.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An operation device, comprising:
a detector configured to detect an operation on a virtual switch by an operator to operate an X-ray irradiation in an X-ray diagnosis apparatus, wherein the virtual switch is impalpable and virtually set at a position settled relatively with respect to the operator; and
output circuitry configured to output a detection result of the operation detected by the detector to the X-ray diagnosis apparatus to be operated,
wherein the virtual switch set at the position settled relatively with respect to the operator is a virtual foot switch, which is subject to a stepping operation executed by the operator, and
the detector is further configured to determine that the stepping operation is executed when a pressure equal to or greater than a threshold value is detected at a pedal position of the virtual foot switch after a foot of the operator moves vertically.

2. The operation device according to claim 1, wherein:
the detector is further configured to detect the stepping operation on the virtual foot switch executed by the operator; and
the output circuitry is further configured to output the detection result of the stepping operation detected by the detector to the X-ray diagnosis apparatus.

3. The operation device according to claim 1, wherein the operation device is further configured to be worn on the operator to operate the X-ray irradiation in the X-ray diagnosis apparatus.

4. The operation device according to claim 3, further comprising a position detector configured to detect a position of the operation device.

5. The operation device according to claim 1, further comprising a vibration device configured to vibrate in accordance with a position of a body portion of the operator for the operation on the virtual switch.

6. The operation device according to claim 5, wherein the vibration device is further configured to vibrate when the body portion of the operator is at an operational position at which the virtual switch is operable.

7. The operation device according to claim 6, wherein the operational position at which the virtual switch is operable is at and/or above the pedal position at which a pedal of the virtual switch is operable.

8. The operation device according to claim 1, wherein the output circuitry is further configured to output the detection result of the operation detected by the detector to an operation device control circuitry provided in the X-ray diagnosis apparatus.

9. The operation device according to claim 8, wherein the output circuitry is further configured to output the detection result of the operation detected by the detector to the operation device control circuitry through wireless communication.

10. An X-ray diagnosis system, comprising:
an X-ray diagnosis apparatus configured to irradiate X-ray X-rays to a subject to obtain a diagnostic image of the subject; and
an operation device configured to operate an X-ray irradiation in the X-ray diagnosis apparatus,
wherein the operation device comprises:
a detector configured to detect an operation on a virtual switch by an operator to operate the X-ray irradiation in the X-ray diagnosis apparatus, wherein the virtual switch is impalpable and virtually set at a position settled relatively with respect to the operator; and
output circuitry configured to output a detection result of the operation detected by the detector to the X-ray diagnosis apparatus to be operated,
wherein the virtual switch set at the position settled relatively with respect to the operator is a virtual foot switch, which is subject to a stepping operation executed by the operator, and
the detector is further configured to determine that the stepping operation is executed when a pressure equal to or greater than a threshold value is detected at a pedal position of the virtual foot switch after a foot of the operator moves vertically.

11. The X-ray diagnosis system according to claim 10, wherein the operation device is further configured to be worn on the operator to operate the X-ray irradiation in the X-ray diagnosis apparatus.

12. The X-ray diagnosis system according to claim 11, further comprising a position detector configured to detect a position of the operation device.

13. The X-ray diagnosis system according to claim 10, further comprising a vibration device configured to vibrate in accordance with a position of a body portion of the operator for the operation on the virtual switch.

14. The X-ray diagnosis system according to claim 13, wherein the vibration device is further configured to vibrate when the body portion of the operator is at an operational position at which the virtual switch is operable.

15. The X-ray diagnosis system according to claim 10, further comprising a display monitor configured to visually display a positional relation between the virtual switch and the body portion of the operator for the operation on the virtual switch.

16. The X-ray diagnosis system according to claim 10, wherein a warning is given to the operator when the position of the virtual switch interferes with other peripheral apparatus.

17. The X-ray diagnosis system according to claim 10, further comprising an operation device control circuitry configured to set the virtual switch at the position settled relatively with respect to the operator.

18. The X-ray diagnosis system according to claim 17, wherein the operation device control circuitry is further configured to hold information on an operational setting for the virtual switch for each operator.

* * * * *